US011679492B2

(12) United States Patent
Roh et al.

(10) Patent No.: US 11,679,492 B2
(45) Date of Patent: *Jun. 20, 2023

(54) LOCKING DEVICE AND MOTION ASSISTANCE APPARATUS INCLUDING THE SAME

(71) Applicant: Samsung Electronics Co., Ltd., Suwon-si (KR)

(72) Inventors: Se-Gon Roh, Suwon-si (KR); Jeonghun Kim, Suwon-si (KR); Minhyung Lee, Seoul (KR); Youn Baek Lee, Yongin-si (KR); Jongwon Lee, Suwon-si (KR); Byungjune Choi, Gunpo-si (KR); Hyun Do Choi, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/686,510

(22) Filed: Mar. 4, 2022

(65) Prior Publication Data

US 2022/0184796 A1 Jun. 16, 2022

Related U.S. Application Data

(63) Continuation of application No. 15/608,120, filed on May 30, 2017, now Pat. No. 11,285,600.

(30) Foreign Application Priority Data

Dec. 8, 2016 (KR) .......................... 10-2016-0166809

(51) Int. Cl.
*B25J 9/00* (2006.01)
*A61F 5/01* (2006.01)
*A61F 2/68* (2006.01)

(52) U.S. Cl.
CPC ........... *B25J 9/0006* (2013.01); *A61F 5/0102* (2013.01); *A61F 2002/6854* (2013.01);
(Continued)

(58) Field of Classification Search
CPC ...... A61H 2003/007; A61H 2201/0192; A61H 2201/1628; A61H 2201/163;
(Continued)

(56) References Cited

U.S. PATENT DOCUMENTS

| 5,662,693 A * | 9/1997 | Johnson .................... A61F 5/01 607/48 |
| 11,285,600 B2 * | 3/2022 | Roh .......................... A61F 2/68 |

(Continued)

FOREIGN PATENT DOCUMENTS

| JP | 08-017623 | 1/1996 |
| JP | 2012-165821 A | 9/2012 |

(Continued)

OTHER PUBLICATIONS

U.S. Appl. No. 15/608,120 filed May 30, 2017; ROH et al.
Korean Notice of Allowance dated Apr. 21, 2023 for KR Application No. 10-2016-0166809.

*Primary Examiner* — Caitlin A Carreiro
(74) *Attorney, Agent, or Firm* — Nixon & Vanderhye P.C.

(57) ABSTRACT

A locking device including a first frame including an insert hole and a first magnetic body, a second frame including an insert recess communicating with the insert hole, and a second magnetic body disposed to face the first magnetic body with a polarity opposite to a polarity of the first magnetic body, and an insert member including a slider inserted into the insert hole and configured to slide relative to the first frame, and a third magnetic body disposed on one side of the slider is provided.

8 Claims, 8 Drawing Sheets

(52) U.S. Cl.
CPC ................ *A61F 2002/6863* (2013.01); *A61F 2005/0158* (2013.01); *A61H 2201/0176* (2013.01); *A61H 2201/165* (2013.01); *A61H 2205/10* (2013.01)

(58) Field of Classification Search
CPC ........ A61H 2201/164; A61H 2201/165; A61H 3/00; A61H 1/0262; A61H 2201/0176; A61H 2205/10; A61F 2005/0146; A61F 2005/0155; A61F 2005/0158; A61F 5/0193; A61F 2002/607; A61F 2002/608; A61F 2/60; A61F 2/604; A61F 2/605; A61F 5/0585; A61F 5/0123; A61F 5/0106; A61F 5/0125; A61F 2002/6854; A61F 2002/6863; A61F 2/68; A61F 5/0102; B65D 43/20; B65D 43/22; B65D 2251/1016; B65D 2313/04; B25J 9/0006

USPC .............. 601/23, 33, 35; 220/812, 833, 230; 602/16, 26, 23

See application file for complete search history.

(56) References Cited

U.S. PATENT DOCUMENTS

| | | | |
|---|---|---|---|
| 2014/0353313 | A1* | 12/2014 | An .......................... A45C 5/02 220/826 |
| 2015/0272764 | A1 | 10/2015 | Kim et al. |
| 2017/0086990 | A1 | 3/2017 | Choi et al. |

FOREIGN PATENT DOCUMENTS

| | | |
|---|---|---|
| KR | 2009-0035139 A | 4/2009 |
| KR | 0460718 | 6/2012 |

* cited by examiner

LOCKING DEVICE AND MOTION ASSISTANCE APPARATUS INCLUDING THE SAME

CROSS-REFERENCE TO RELATED APPLICATION

This application is a Continuation of U.S. application Ser. No. 15/608,120, filed May 30, 2017, which claims priority to KR-10-2016-0166809, filed on Dec. 8, 2016, the entire contents of which are all hereby incorporated herein by reference in their entireties.

BACKGROUND

1. Field

At least one example embodiment relates to a locking device and/or a motion assistance apparatus including the locking device.

2. Description of the Related Art

Motion assistance apparatuses may enable the elderly and/or patients having joint problems to walk with less effort, and may increase muscular strength of users, for example, for military purposes.

SUMMARY

Some example embodiments relate to a locking device.

In some example embodiments, the locking device includes a first frame having an insert hole therein, the first frame including a first magnetic body; a second frame having an insert recess therein, the second frame including a second magnetic body having a polarity opposite to a polarity of the first magnetic body, the second magnetic body configured to face the first magnetic body such that the insert recess corresponds to the insert hole, if the first frame is connected to the second frame; and an insert member including a slider and a third magnetic body, the slider configured to slide relative to the first frame in the insert hole, the third magnetic body being on the slider.

In some example embodiments, when the first frame is connected to the second frame and the insert member is inserted into the first frame through the insert hole by at least a first length, a repulsive force between the second magnetic body and the third magnetic body encourages the insert member to travel towards a bottom of the insert recess.

In some example embodiments, when the insert member is inserted into the first frame in an insertion direction through the insert hole by an amount less than or equal to a second length, a repulsive force is exerted between the first magnetic body and the third magnetic body, the second length being less than the first length.

In some example embodiments, the insert member further includes a protrusion protruding perpendicular to the insertion direction of the slider, and the first frame further includes a stepped portion configured to contact the protrusion when the insert member slides more than a set amount in a direction opposite the insertion direction to block separation of the insert member from the locking device.

In some example embodiments, the insert member further includes a connecting member and an adjuster, the connecting member configured to protrude a protruding amount from the slider, and the adjuster configured to adjust a length of the protruding amount, and the second frame further has a connecting recess therein, the connecting member configured to connect to the second frame via the connecting recess.

In some example embodiments, the second frame further includes a fourth magnetic body in the insert recess such that the fourth magnetic body faces the third magnetic body, if the insert member is inserted into the insert recess, the fourth magnetic body having a polarity opposite to a polarity of the third magnetic body.

In some example embodiments, the first frame further includes a fifth magnetic body, and the second frame further includes a sixth magnetic body configured to face the fifth magnetic body, if the first frame is connected to the second frame, the sixth magnetic body having a polarity opposite to a polarity of the fifth magnetic body.

In some example embodiments, the first frame further includes a connecting plate configured to guide the first frame to move in a set direction when the first frame connects and separates from the second frame.

Other embodiments relate to a motion assistance apparatus.

In some example embodiment, the motion assistance apparatus includes a proximal support configured to support a proximal part of a user; a distal support configured to support a distal part of the user; and a locking device including, a first frame connected to the proximal support, the first frame having an insert hole therein, the first frame including a first magnetic body, a second frame connected to the distal support, the second frame including a second magnetic body having a polarity opposite to a polarity of the first magnetic body, the second magnetic body configured to face the first magnetic body if the first frame is connected to the second frame, and an insert member including a slider and a third magnetic body, the slider configured to slide relative to the first frame in the insert hole, the third magnetic body being on the slider.

In some example embodiments, the second frame further includes a fourth magnetic body configured to face the third magnetic body, if the insert member is inserted into the insert hole, the fourth magnetic body having a polarity opposite to a polarity of the third magnetic body.

In some example embodiments, when the insert member is spaced apart from the first frame toward the second frame by at least a first length, a repulsive force is exerted between the third magnetic body and the second magnetic body and an attractive force is exerted between the third magnetic body and the fourth magnetic body such that the insert member is encouraged into an insert recess in the second frame.

In some example embodiments, the insert member further includes a connecting member and an adjuster, the connecting member configured to protrude a protruding amount from the first end of the slider, and the adjuster configured to adjust a length of the protruding amount, the second frame further has a connection recess herein, the connecting member configured to connect to the second frame via the connection recess, and the adjuster is configured to rotate to connect the connecting member to the connection recess when the insert member is inserted into the insert recess.

In some example embodiments, when the insert member is inserted into the first frame in an insertion direction an amount less than or equal to a second length, a repulsive force is exerted between the first magnetic body and the third magnetic body.

In some example embodiments, the insert member further includes a protrusion protruding perpendicular to the insertion direction of the slider, the first frame further includes a stepped portion configured to contact the protrusion when the insert member slides more than a set amount in a direction opposite the insertion direction to block separation of the insert member from the locking device when the repulsive force is exerted between the first magnetic body and the third magnetic body.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Figure 1:
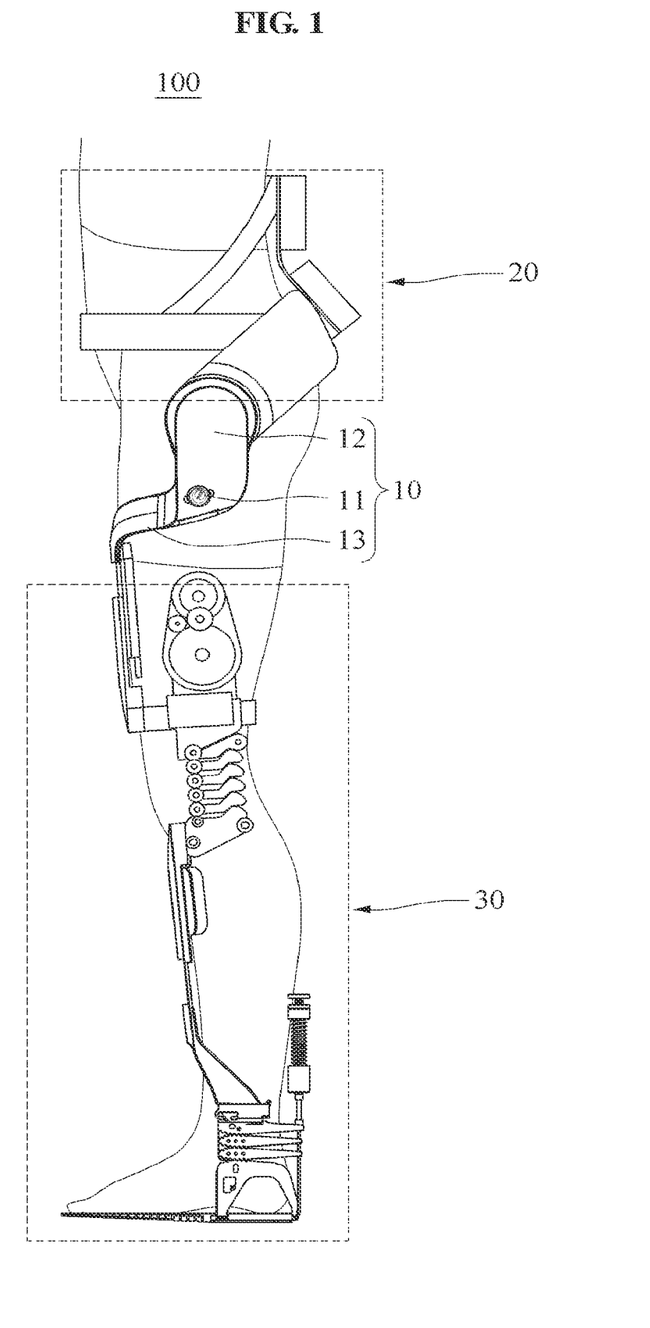
FIG. 1 is a side view illustrating a motion assistance apparatus according to at least one example embodiment.

FIG. 1 is a side view illustrating a motion assistance apparatus according to at least one example embodiment.

Referring to FIG. 1, a motion assistance apparatus 100 may be worn by a user in order to assist a motion of the user. The user may be a human, an animal, a robot or any other moving structure or being. However, example embodiments are not limited thereto. The motion assistance apparatus 100 may include a locking device 10, a proximal support 20, and a distal support 30.

The proximal support 20 and the distal support 30 may be disposed on opposite sides relative to one portion of a user to support a proximal part and a distal part, respectively. For example, the proximal support 20 and the distal support 30 may be disposed on opposite sides relative to a thigh of the user. The proximal support 20 may support a portion above the thigh, for example, a waist and/or a pelvis. The distal support 30 may support a portion below the thigh, for example, a knee, a calf, and/or a foot. The proximal support 20 may include a detachable belt to fully support the waist of the user. The distal support 30 may include a detachable belt to fully support an upper portion of the knee of the user, and may be provided in a structure that encloses top and bottom sides of the foot to support the foot of the user.

The proximal support 20 and the distal support 30 may be disposed on opposite sides relative to an upper arm of the user. The proximal support 20 may support, for example, a shoulder and/or a back. The distal support 30 may support, for example, a forearm. The proximal support 20 may include a detachable belt to fully support the shoulder of the user. The distal support 30 may include a detachable belt to fully support the forearm of the user or may be provided in a structure that encloses the forearm.

The locking device 10 may connect the proximal support 20 and the distal support 30 or separate the proximal support 20 from the distal support 30. For example, the motion assistance apparatus 100 may be separable using the locking device 10. The locking device 10 may be provided in, for example, a portion that covers the thigh of the user, of the motion assistance apparatus 100. The user may easily wear or detach the motion assistance apparatus 100 using the locking device 10. For example, the user may wear one of the proximal support 20 and the distal support 30, wear remaining one of the proximal support 20 and the distal support 30, and then connect the proximal support 20 and the distal support 30 using the locking device 10. The proximal support 20 and the distal support 30 connected by the locking device 10 may transmit or receive power to or from each other. The locking device 10 may include an insert member 11, a first frame 12, and a second frame 13.

The first frame 12 and the second frame 13 may be connected to or separated from each other. Also, the first frame 12 and the second frame 13 may be firmly connected to each other using a separate member, for example, the insert member 11. As illustrated in FIG. 1, each of the first frame 12 and the second frame 13 may be an element of a thigh frame of the motion assistance apparatus 100. The first frame 12 and the second frame 13 are not limited as elements of the motion assistance apparatus 100 and may also be elements that may need to be connected and separated in another configuration. For example, the first frame 12 and the second frame 13 may be respectively connected to a case and a cover of an openable safety deposit box. The locking device 10 may be applied to a storage such as a safety deposit box. Hereinafter, a case in which the first frame 12 and the second frame 13 are used as a thigh frame of the motion assistance apparatus 100 will be described.

The first frame 12 may be rotatably connected to the proximal support 20. For example, the first frame 12 may be rotatably hinged to one end of the proximal support 20. In this example, the first frame 12 may rotate in response to a movement of a hip joint of the user. In response to a flexion or an extension of the hip joint, an angle between the first frame 12 and the proximal support 20 may be changed based on a flexion or extension angle.

The second frame 13 may be connected to the distal support 30. The second frame 13 may cover at least a portion of the thigh including a portion that is curved toward a front side of the thigh of the user based on a shape of the thigh. For example, an end portion of the second frame 13 may be located on a front surface of the thigh. In this example, a force transmitted from the second frame 13 toward the thigh may be effectively transmitted. Also, a force applied from the thigh toward the second frame 13 may be effectively transmitted to the second frame 13.

Figure 2:
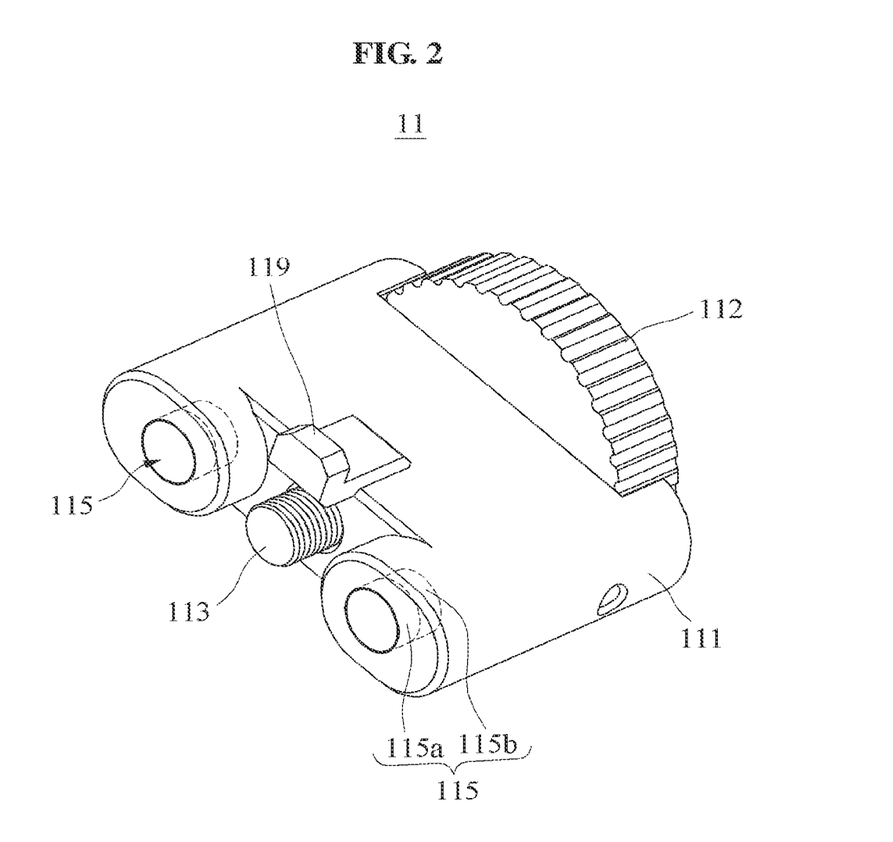
FIG. 2 is a perspective view illustrating an insert member according to at least one example embodiment.
Figure 3:
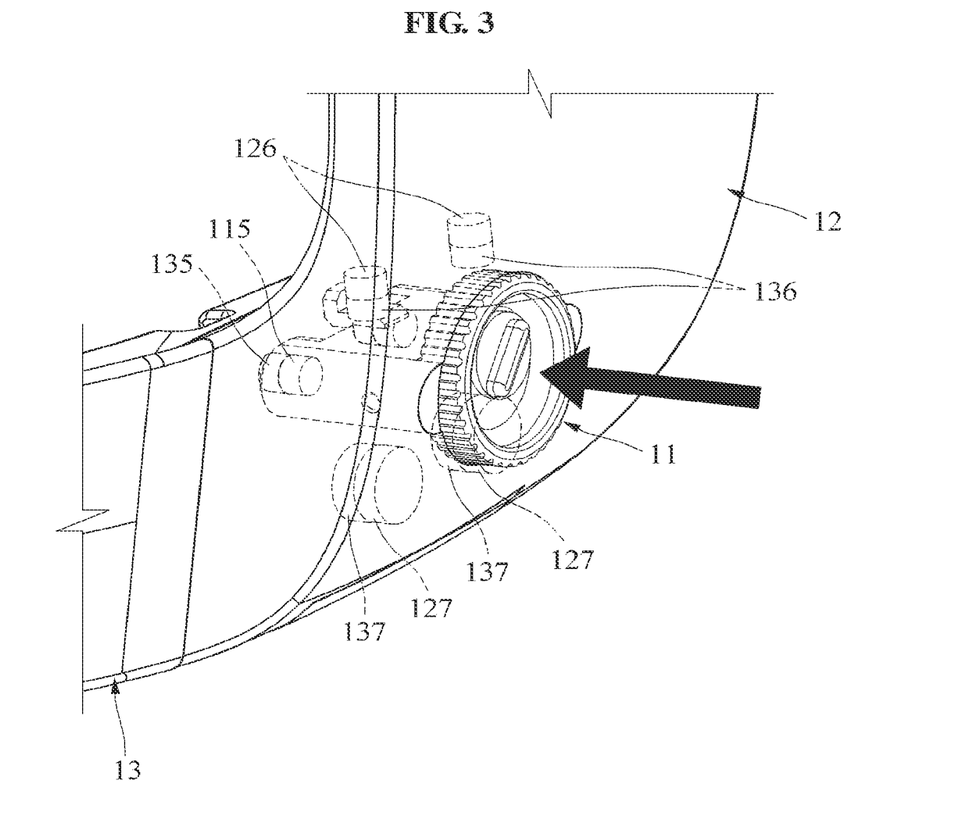
FIG. 3 is an enlarged view illustrating a locking device including an insert member inserted into a first frame and a second frame according to at least one example embodiment.
Figure 4:
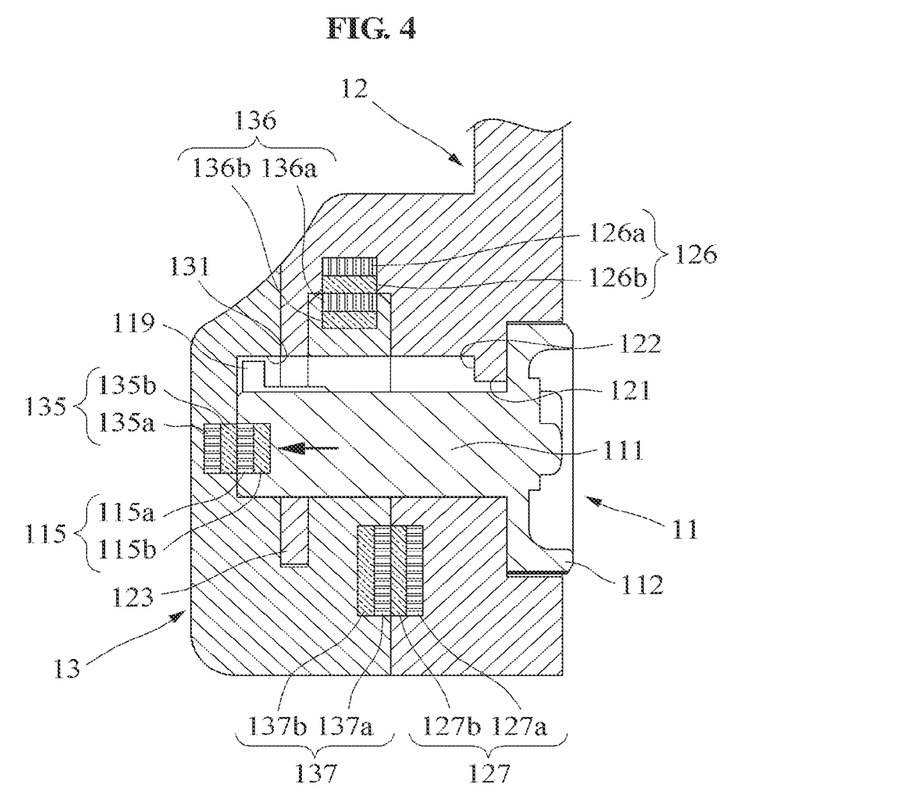
FIG. 4 is a cross-sectional view illustrating a locking device including an insert member inserted into a first frame and a second frame according to at least one example embodiment.

FIG. 2 is a perspective view illustrating an insert member according to at least one example embodiment, FIG. 3 is an enlarged view illustrating a locking device including an insert member inserted into a first frame and a second frame according to at least one example embodiment, and FIG. 4 is a cross-sectional view illustrating a locking device including an insert member inserted into a first frame and a second frame according to at least one example embodiment.

Referring to FIGS. 2 through 4, the locking device 10 may include the first frame 12, the second frame 13, and the insert member 11.

The first frame 12 may include an insert hole 121, a stepped portion 122, a connecting plate 123, a first magnetic body 127, and a fifth magnetic body 126.

The insert hole 121 may be a hole through which the insert member 11 passes. For example, the insert hole 121 may have the same shape as an outer shape of a portion in which the insert member 11 slides while the insert member 11 is inserted into the insert hole 121. Also, the insert hole 121 may be provided in a size having an offset with respect to the outer shape such that the insert member 11 passes smoothly. In such structure, the insert member 11 may be inserted into the insert hole 121 and allowed to slide smoothly. The insert hole 121 may be provided in, for example, a form that is elongated vertically to the longitudinal direction of the first frame 12. The insert hole 121 may also be provided, for example, in a form of a slot that extends vertically to the longitudinal direction of the first frame 12 and has fillet-processed vertices. A form of the insert hole 121 is not limited to the aforementioned examples and thus, various forms are applicable to the insert hole 121.

The stepped portion 122 may reduce a probability of (or, alternatively, prevent) a separation of the insert member 11 from the first frame 12. The stepped portion 122 may be formed on an inner side of the first frame 12 such that a portion of the insert member 11 is locked by the stepped portion 122.

The first magnetic body 127 may have a magnetic property. The first magnetic body 127 may be, for example, a permanent magnet having a north (N) pole 127a and a south (S) pole 127b, or an electromagnet operating by a current applied from an external source. The first magnetic body 127 may be, for example, a neodymium magnet, a ferrite magnet, a samarium cobalt magnet, and an alnico magnet. The first magnetic body 127 may be, for example, a circular magnet. Hereinafter, a magnetic body may have the same property as that of the first magnetic body 127.

The first magnetic body 127 may be disposed inside the first frame 12. The first magnetic body 127 may be disposed such that a facing direction of the N pole 127a and the S pole 127b of the first magnetic body 127 is vertical to a longitudinal direction of the first frame 12. For example, the S pole 127b of the first magnetic body 127 may be disposed to face the second frame 13 that is attachable to the first frame 12. The plurality of first magnetic bodies 127 may be provided to increase a connection force between the first frame 12 and the second frame 13. The plurality of first magnetic bodies 127 may be spaced apart from one another vertically to the longitudinal direction of the first frame 12. In an example of FIG. 3, two first magnetic bodies 127 may be provided to be spaced apart from each other. When the second frame 13 includes a magnetic body and an attractive force is exerted between the magnetic body and the first magnetic body 127, a force connecting the first frame 12 and the second frame 13 in a direction vertical to the longitudinal direction of the first frame 12 may be applied to the first frame 12 and the second frame 13.

The fifth magnetic body 126 may be disposed vertically to the first magnetic body 127. A facing direction of an N pole 126a and an S pole 126b of the fifth magnetic body 126 may be vertical to the facing direction of the N pole 127a and the S pole 127b of the first magnetic body 127. The fifth magnetic body 126 may be disposed on an opposite side to the first magnetic body 127 relative to the insert hole 121. When the second frame 13 includes a magnetic body and an attractive force is exerted between the magnetic body and the fifth magnetic body 126, a force connecting the first frame 12 and the second frame 13 in the longitudinal direction of the first frame 12 may be applied to the first frame 12 and the second frame 13. Likewise, the fifth magnetic body 126 may also provide the force connecting the first frame 12 and the second frame 13 in the direction different from the direction in which the first magnetic body 127 is disposed and thus, the connection force between the first frame 12 and the second frame 13 may increase.

The connecting plate 123 may be inserted into a slot formed on the second frame 13. The connecting plate 123 may guide the first frame 12 and the second frame 13 to be connected or separated in one direction. The connecting plate 123 may reduce a probability of (or, alternatively, prevent) the first frame 12 and the second frame 13 from being connected or separated in a direction other than the one direction. Through this, the connecting plate 123 may structurally increase the connection force between the first frame 12 and the second frame 13. The connecting plate 123 may be a plate-type member configured to be inserted into the second frame 13. As illustrated in FIG. 4, the connecting plate 123 may extend in the longitudinal direction of the first frame 12 to be inserted into the slot formed on the second frame 13.

The insert member 11 may be inserted into an insert recess 131 of the second frame 13 via the insert hole 121 of the first frame 12. When the first frame 12 is connected to the second frame 13, the insert member 11 may be inserted to the insert recess 131 via the insert hole 121 such that the first frame 12 is firmly connected to the second frame 13 and the first frame 12 is less likely to (or, alternatively, prevented) from separating from the second frame 13. When the first frame 12 is separated from the second frame 13, the insert member 11 may slide into the insert hole 121.

The insert member 11 may include a slider 111, an adjuster 112, a connecting member 113, a third magnetic body 115, and a protrusion 119.

The slider 111 may slide relative to the first frame 12. The slider 111 may be inserted into the insert hole 121 of the first frame 12 and slide relative to the first frame 12. The slider 111 may assist the first frame 12 and the second frame 13 to be continually connected without separation. For example, when the first frame 12 and the second frame 13 are connected in parallel to a direction of gravity, the slider 111 may apply a force toward the second frame 13 in a direction opposite to the direction of gravity, so as to reduce a probability of (or, alternatively, prevent) the second frame 13 from separating from the first frame 12 due to a gravity.

The connecting member 113 may be connected to the second frame 13. The connecting member 113 may penetrate the slider 111 and protrude from one side of the slider 111. For example, one end of the connecting member 113 may protrude from a front face of the slider 111 in a direction in which the slider 111 inserted into the insert hole 121. The connecting member 113 may be, for example, a bolt tap having a screw thread.

The adjuster 112 may adjust a length to which the connecting member 113 protrudes from the slider 111. The adjuster 112 and the connecting member 113 may operate based on, for example, a ball screw mechanism. When the adjuster 112 rotates in one direction, the length to which the connecting member 113 protrudes from the slider 111 may increase. When the adjuster 112 rotates in the other direction, the length to which the connecting member 113 protrudes from the slider 111 may decrease.

The adjuster 112 may be provided in a shape easily gripped by a user. The adjuster 112 may be in a circular shape with a size easy to be gripped by the user, for example, a diameter between 2 and 5 centimeters (cm). Also, the adjuster 112 may have a shape curved along a circumferential face. The curved shape may increase a frictional force between a hand of the user and the adjuster 112 and reduce a probability of (or, alternatively, prevent) the hand from slipping when the user rotates the adjuster 112.

The third magnetic body 115 may be disposed on one side of the slider 111. The third magnetic body 115 may be disposed on a front face of the slider 111 such that a facing direction of an N pole 115a of the third magnetic body 115 is the same as a direction in which the slider 111 is inserted into the insert hole 121. An S pole 115b of the third magnetic body 115 may be toward the adjuster 112. For example, the N pole 115a of the third magnetic body 115 may be disposed to face the second frame 13. The third magnetic bodies 115 may be provided to increase a magnetic force exerted between the insert member 11 and the second frame 13. For example, two third magnetic bodies 115 may be disposed on opposite sides relative to the connecting member 113, respectively.

The protrusion 119 may be locked by the first frame 12 to reduce a probability of (or, alternatively, prevent) a separation of the insert member 11 from the first frame 12. The protrusion 119 may protrude vertically to an insertion direction of the slider 111. For example, the protrusion 119 may be provided in an L-shape and disposed on an upper face of the slider 111. The first frame 12 may include the stepped portion 122 formed inward the insert hole 121 and configured to lock the protrusion 119. The insert hole 121 of the first frame 12 and the insert recess 131 of the second frame 13 may each include a portion to which the protrusion 119 is slidably connected.

Figure 7:
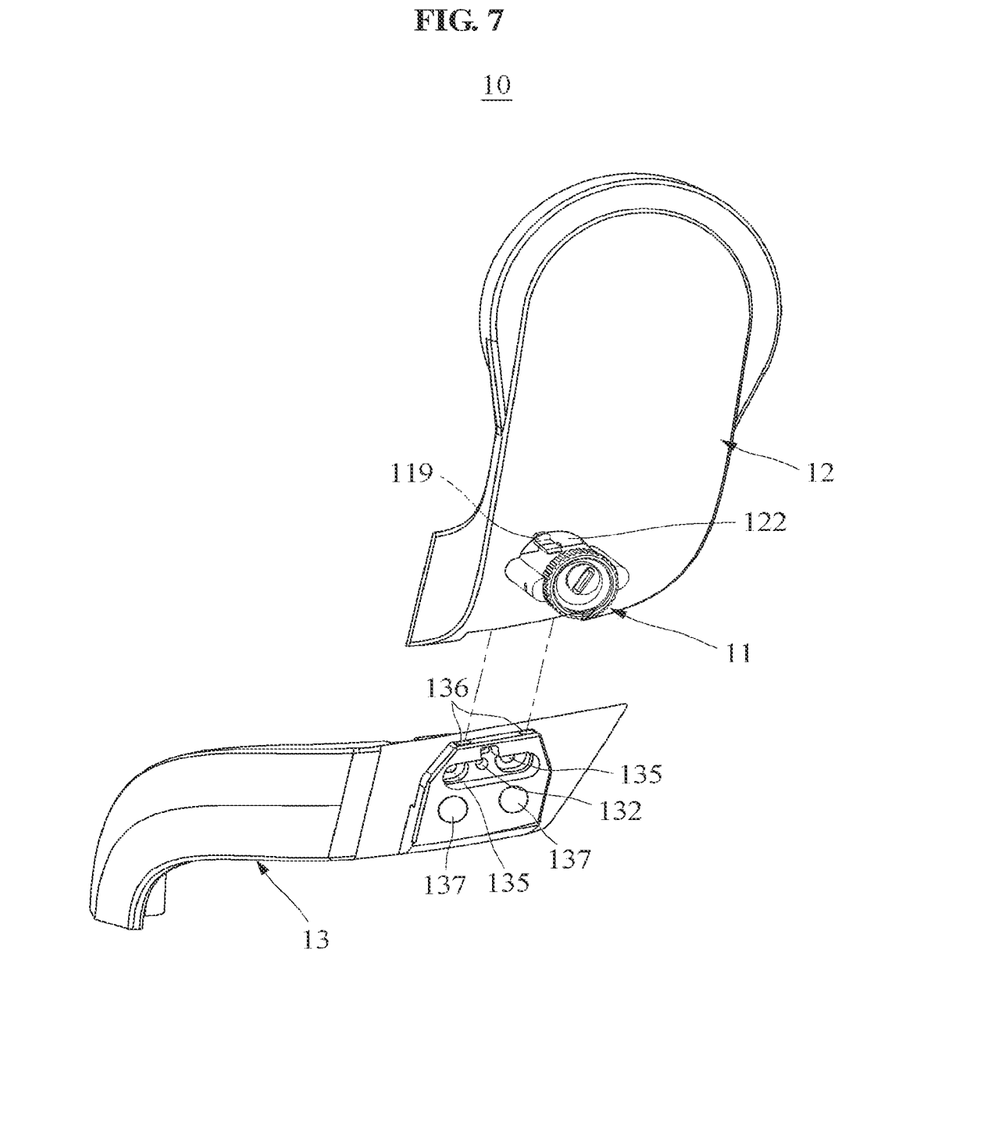
FIG. 7 is a perspective view illustrating a case in which a first frame is separated from a second frame according to at least one example embodiment.

The second frame 13 may include the insert recess 131, a connecting recess 132 as further discussed in FIG. 7, a second magnetic body 137, a fourth magnetic body 135, and a sixth magnetic body 136.

The insert recess 131 may communicate with the insert hole 121 of the first frame 12. The insert recess 131 may have a room to receive the insert member 11. The insert member 11 may be inserted to reach a bottom face of the insert recess 131 via the insert hole 121 and fully connected to the second frame 13. The bottom face may be a face in contact with a front face of the insert member 11 when the insert member 11 is fully inserted into the insert recess 131.

The connecting recess 132 may be in a structure to be connected to the connecting member 113 of the insert member 11. For example, when the connecting member 113 is a bolt tap having a screw thread, the connecting recess 132 may have a shape corresponding to the screw thread of the bolt tap. The connecting recess 132 may be disposed on the bottom face of the insert recess 131 to face the connecting member 113.

The second magnetic body 137 may be provided in the second frame 13 to face the first magnetic body 127. The second magnetic body 137 may be disposed such that an N pole 137a of the second magnetic body 137 is toward the S pole 127b of the first magnetic body 127. In this example, when the first frame 12 is connected to the second frame 13, an attractive force may be exerted between the second magnetic body 137 and the first magnetic body 127 and thus, the connection force between the first frame 12 and the second frame 13 may increase. When the plurality of first magnetic bodies 127 are provided, the plurality of second magnetic bodies 137 corresponding to the number of first magnetic bodies 127 may also be provided. In an example of FIG. 3, two first magnetic bodies 127 and two second magnetic bodies 137 may be arranged vertically to the longitudinal direction of the first frame 12. In this example, the two first magnetic bodies 127 may be spaced apart from each other and the two second magnetic bodies 137 may be spaced apart from each other.

The fourth magnetic body 135 may be disposed to face the third magnetic body 115 with a polarity opposite to a polarity of the third magnetic body 115. The fourth magnetic body 135 may be provided in the insert recess 131 such that an S pole 135b of the fourth magnetic body 135 faces the third magnetic body 115. When the insert member 11 is inserted to the insert recess 131, the third magnetic body 115 may be pulled by an attractive force. When the third magnetic body 115 is in a predetermined distance from the fourth magnetic body 135, an attractive force may be exerted between the third magnetic body 115 and the fourth magnetic body 135, and the third magnetic body 115 may be pulled toward the fourth magnetic body 135. The predetermined distance may be a distance to which a magnetic force of the fourth magnetic body 135 is exerted. In this example, the insert member 11 may be automatically inserted into the insert recess 131. Also, the fourth magnetic body 135 may use the attractive force between the fourth magnetic body 135 and the third magnetic body 115 to increase a force connecting the insert member 11 to the second frame 13. When the plurality of third magnetic bodies 115 are arranged, for example, the two third magnetic bodies 115 are respectively disposed on opposite sides relative to the connecting member 113, the plurality of fourth magnetic bodies 135 may each be disposed to face a magnetic pole of the corresponding third magnetic body 115.

The sixth magnetic body 136 may be disposed to face the fifth magnetic body 126 with a polarity opposite to a polarity of the fifth magnetic body 126. When the S pole 126b of the fifth magnetic body 126 is disposed toward a bottom of the first frame 12 based on the longitudinal direction of the first frame 12, the sixth magnetic body 136 may be disposed to face the fifth magnetic body 126 such that an N pole 136a of the sixth magnetic body 136 is toward a top of the first frame 12 based on the longitudinal direction of the first frame 12. An attractive force between the sixth magnetic body 136 and the fifth magnetic body 126 may increase the connection force between the first frame 12 and the second frame 13.

A magnetic force between the second magnetic body 137 and the third magnetic body 115 and a magnetic force between the fourth magnetic body 135 and the third magnetic body 115 may be used for the insert member 11 to be inserted to the insert hole 121 and the insert recess 131 and automatically slide therein.

When the first frame 12 is connected to the second frame 13, and when the insert member 11 is inserted into the first frame 12 via the insert hole 121 by at least a first preset length, a repulsive force between the second magnetic body 137 and the third magnetic body 115 may allow the insert member 11 to be inserted toward a bottom of the insert recess 131. The first preset length may be a vertical distance to which the second magnetic body 137 is spaced from an outer face of the first frame 12. For example, when the insert member 11 is inserted into the first frame 12 by at least the first preset length, the third magnetic body 115 may move in a direction as indicated by an arrow of FIG. 4, so as to be located leftward relative to the second magnetic body 137. In this example, due to a repulsive force between the S pole 115b of the third magnetic body 115 and an S pole 137b of the second magnetic body 137, the third magnetic body 115 may be slid via the insert hole 121 and the insert recess 131 in the direction as indicated by the arrow of FIG. 4.

When the first frame 12 is connected to the second frame 13, and when the insert member 11 is inserted via the insert hole 121, the attractive force between the fourth magnetic body 135 and the third magnetic body 115 may allow the insert member 11 to be inserted toward the bottom of the insert recess 131. In this example, due to an attractive force between the N pole 115a and the third magnetic body 115 and the S pole 135b of the fourth magnetic body 135, the insert member 11 may be slid via the insert hole 121 and the insert recess 131 in the direction as indicated by the arrow of FIG. 4.

The user may easily insert the insert member 11 into the insert recess 131 using the repulsive force between the second magnetic body 137 and the third magnetic body 115 and the attractive force between the fourth magnetic body 135 and the third magnetic body 115. The insert member 11 may be inserted to the bottom the insert recess 131 by the magnetic force although the user does not fully insert the insert member 11 to reach the bottom of the insert recess 131.

Figure 5:
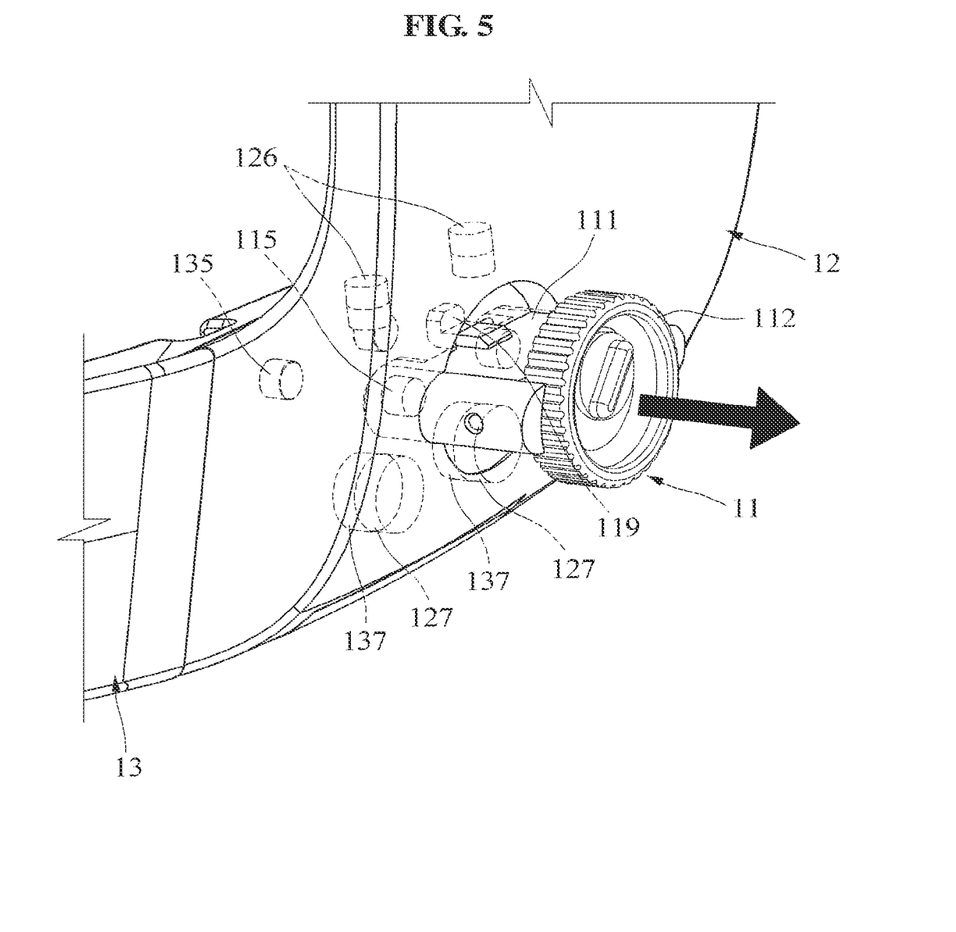
FIG. 5 is an enlarged view illustrating a case in which a protrusion of an insert member is locked by a stepped portion of a first frame according to at least one example embodiment.
Figure 6:
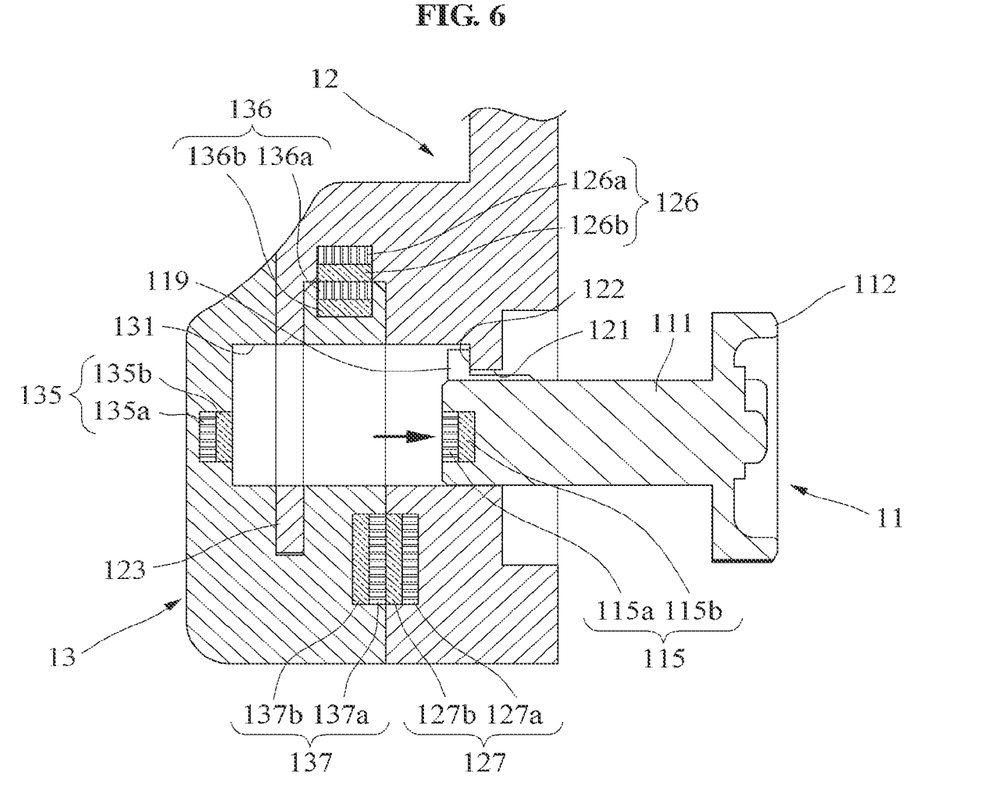
FIG. 6 is a cross-sectional view illustrating a case in which a protrusion of an insert member is locked by a stepped portion of a first frame according to at least one example embodiment.

FIG. 5 is an enlarged view illustrating a case in which a protrusion of an insert member is locked by a stepped portion of a first frame according to at least one example embodiment, and FIG. 6 is a cross-sectional view illustrating a case in which a protrusion of an insert member is locked by a stepped portion of a first frame according to at least one example embodiment.

Referring to FIGS. 5 and 6, the first frame 12 may include the insert hole 121, the stepped portion 122, the first magnetic body 127, the fifth magnetic body 126, and the connecting plate 123. The second frame 13 may include the insert recess 131, the connecting recess 132, the second magnetic body 137, the fourth magnetic body 135, and the sixth magnetic body 136. The insert member 11 may include the slider 111, the adjuster 112, the connecting member 113, the third magnetic body 115, and the protrusion 119.

A magnetic force between the first magnetic body 127 and the third magnetic body 115 may be used for the insert member 11 to be inserted to the insert hole 121 and the insert recess 131 and automatically slide therein.

When the first frame 12 is connected to the second frame 13, and when the insert member 11 is inserted into the first frame 12 via the insert hole 121 within a second desired (or, alternatively, preset) length that is less than a first desired (or, alternatively, preset) length, a repulsive force may be exerted between the first magnetic body 127 and the third magnetic body 115. The second preset length may be a vertical distance to which the first magnetic body 127 is spaced apart from an outer face of the first frame 12. For example, when the insert member 11 is inserted into the first frame 12 within the second preset length, the third magnetic body 115 may move in a direction as indicated by an arrow of FIG. 6, so as to be located rightward relative to the first magnetic body 127. In this example, due to a repulsive force between the N pole 115a of the third magnetic body 115 and the N pole 127a of the first magnetic body 127, the insert member 11 may be slid via the insert hole 121 in the direction indicated by the arrow of FIG. 6. The insert member 11 may slide until the protrusion 119 is in contact with the stepped portion 122. When the protrusion 119 is in contact with the stepped portion 122, the protrusion 119 may be continually in contact with the stepped portion 122 in the insert member 11 by the repulsive force between the N pole 115a of the third magnetic body 115 and the N pole 127a of the first magnetic body 127.

A user may easily slide the insert member 11 using a magnetic force between the first magnetic body 127 and the third magnetic body 115. Although the user does not slide the insert member 11 until the protrusion 119 is in contact with the stepped portion 122, the insert member 11 may be slid by the repulsive force between the first magnetic body 127 and the third magnetic body 115 until the protrusion 119 is in contact with the stepped portion 122. The repulsive force between the first magnetic body 127 and the third magnetic body 115 may be consistently applied to allow the insert member 11 to be maintained in contact with the stepped portion 122. Also, the repulsive force may reduce a probability of (or, alternatively, prevent) the insert member 11 from being easily affected by, for example, a vibration of the first frame 12. The repulsive force between the first magnetic body 127 and the third magnetic body 115 may reduce a probability of (or, alternatively, prevent) the insert member 11 from being located between the first frame 12 and the second frame 13. Through this, the user may easily connect and separate the first frame 12 to and from the second frame 13.

Figure 8:
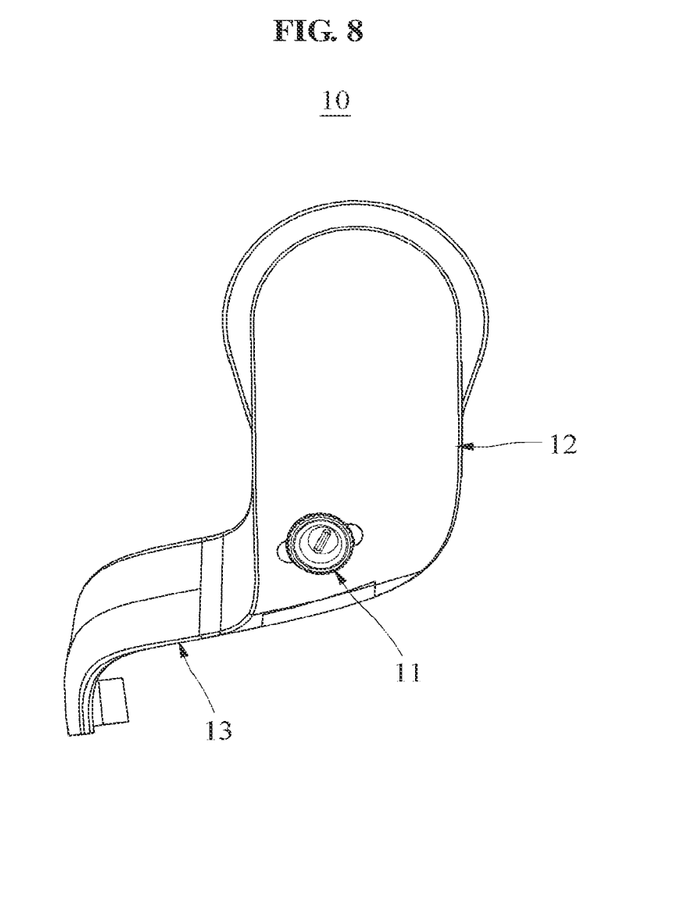
FIG. 8 is a side view illustrating a case in which a first frame is separated from a second frame according to at least one example embodiment.

FIG. 7 is a perspective view illustrating a case in which a first frame is separated from a second frame according to at least one example embodiment, and FIG. 8 is a side view illustrating a case in which a first frame is separated from a second frame according to at least one example embodiment.

Since the description of FIG. 4 is also applicable here, repeated description of the first frame 12, the second frame 13, and the insert member 11 will be omitted.

Referring to FIGS. 7 and 8, a user may connect the first frame 12 and the second frame 13 by moving the first frame 12 and the second frame 13 in one direction. Before the first frame 12 is connected to the second frame 13, the protrusion 119 of the insert member 11 may be in contact with the stepped portion 122 by a repulsive force between the first magnetic body 127 and the third magnetic body 115. The user may connect the first frame 12 and the second frame 13, rotate the adjuster 112, and then connect the connecting member 113 to the connecting recess 132.

When the first frame 12 is separated from the second frame 13, the insert member 11 may be restricted on sliding via the insert hole 121 due to the repulsive force between the first magnetic body 127 and the third magnetic body 115. For example, the protrusion 119 of the insert member 11 may be in contact with the stepped portion 122. The user may connect the first frame 12 and the second frame 13 without an interference of the insert member 11.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus comprising:
    a proximal support configured to be worn on a proximal part of a user;
    a distal support configured to be worn on a distal part of the user; and
    a locking device including,
        a first frame connected to the proximal support, the first frame having an insert hole therein, the first frame including a first magnetic body,
        a second frame connected to the distal support, the second frame including a second magnetic body having a polarity opposite to a polarity of the first magnetic body, the second magnetic body configured to face the first magnetic body if the first frame is connected to the second frame, and
        an insert member including a slider and a third magnetic body, the slider configured to slide relative to the first frame in the insert hole, the third magnetic body being on a first end of the slider,
        wherein the insert member further includes a connector and an adjuster, wherein the connector is configured to protrude a protruding amount from the slider, and the adjuster is configured to adjust a length of the protruding amount, and
        the second frame further includes a connecting recess therein, the connector configured to connect to the second frame via at least the connecting recess.

2. The motion assistance apparatus of claim 1, wherein when the insert member is inserted into the first frame in an insertion direction an amount less than or equal to a second length, a repulsive force is exerted between the first magnetic body and the third magnetic body.

3. The motion assistance apparatus of claim 2, wherein
    the insert member further includes a protrusion protruding perpendicular to the insertion direction of the slider, and
    the first frame further includes a stepped portion configured to contact the protrusion when the insert member slides more than a set amount in a direction opposite the insertion direction to block separation of the insert member from the locking device when the repulsive force is exerted between the first magnetic body and the third magnetic body.

4. A locking device comprising:
    a first frame having an insert hole therein, the first frame including a first magnetic body;
    a second frame having an insert recess therein, the second frame including a second magnetic body having a polarity opposite to a polarity of the first magnetic body, the second magnetic body configured to face the first magnetic body such that the insert recess corresponds to the insert hole, if the first frame is connected to the second frame; and
    an insert member including a slider and a third magnetic body, the slider configured to slide relative to the first frame in the insert hole, the third magnetic body being on the slider,
    wherein the insert member further includes a connector and an adjuster, wherein the connector is configured to protrude a protruding amount from the slider, and the adjuster is configured to adjust a length of the protruding amount, and
    the second frame further includes a connecting recess therein, the connector configured to connect to the second frame via at least the connecting recess.

5. The locking device of claim 4, wherein when the first frame is connected to the second frame and the insert member is inserted into the first frame through the insert hole by at least a first length, a repulsive force between the second magnetic body and the third magnetic body encourages the insert member to travel towards a bottom of the insert recess.

6. The locking device of claim 5, wherein when the insert member is inserted into the first frame in an insertion direction through the insert hole by an amount less than or equal to a second length, a repulsive force is exerted between the first magnetic body and the third magnetic body, the second length being less than the first length.

7. The locking device of claim 6, wherein
    the insert member further includes a protrusion protruding perpendicular to the insertion direction of the slider, and
    the first frame further includes a stepped portion configured to contact the protrusion when the insert member slides more than a set amount in a direction opposite the insertion direction to block separation of the insert member from the locking device.

8. The locking device of claim 4, wherein the first frame further comprises:
   a connecting plate configured to guide the first frame to move in a set direction when the first frame connects and separates from the second frame.

\* \* \* \* \*